Figure 1:
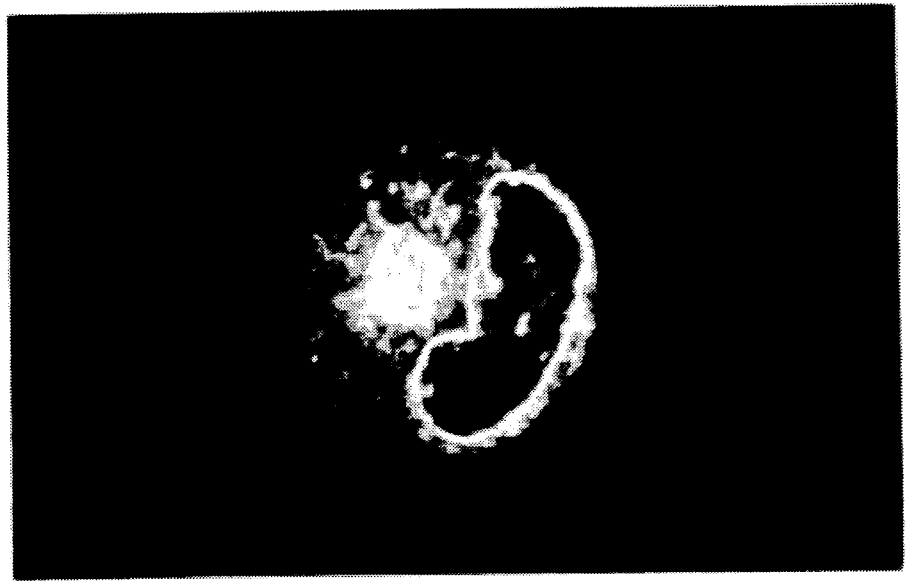

United States Patent [19]

Doglia et al.

[11] Patent Number: 5,580,750
[45] Date of Patent: Dec. 3, 1996

[54] METHOD FOR THE DIAGNOSIS OF MULTIDRUG RESISTANCE IN LIVING CELLS

[76] Inventors: Silvia M. Doglia, 2, Via P. Maestri, I 20129 Milan; Anna M. Villa, 6, Via Gambirasio, I 24068 Seriate, Bergamo, both of Italy; Michel Manfait, 5 rue des Moissons, F 51100 Reims, France

[21] Appl. No.: 43,292

[22] Filed: Apr. 6, 1993

[30] Foreign Application Priority Data

Apr. 6, 1992 [IT] Italy ..................... MI92A0829

[51] Int. Cl.[6] ............... C12Q 1/18; C12Q 1/00; G01N 21/00
[52] U.S. Cl. .................. 435/32; 435/4; 435/29; 435/968; 436/164; 436/172
[58] Field of Search ................ 435/29, 32, 4, 435/968; 436/172, 164

[56] References Cited

U.S. PATENT DOCUMENTS 5,179,276  1/1993  Hikamata ................. 250/234

OTHER PUBLICATIONS

Zweiev et al Biochimica et Biophysica Acta 884 (1986) pp. 326–516.
Giglii et al. Biochem et Biophysica Acta 950 (1988) 13–20.
Gervasoni, et al. Cancer Research 51, 4955–4963 (1991).
Kessel, et al. Cancer Research 51, 4665–4670 (1991).
Neyfakh, "Use of Fluorescent Dyes as Molecular Probes for the Study of Multidrug Resistance", *Academic Press, Inc.*, 174, 168–176 (1988).
de Lange et al., "Quantification by Laser Scan Microscopy of Intracellular Doxorubicin Distribution", *Cytometry*, 13, 572–576 (1992).
Hindenburg et al., "Intracellular Distribution and Pharmacokinetics of Daunorubicin in Anthracycline–sensitive and —resistant HL-60 Cells", *Cancer Research*, 49, 4607–4614 (1989).
Nabiev et al., "Selective Analysis of Antitumor Drug Interaction with Living Cancer Cells as Probed by Surface-Enhanced Raman Spectroscopy," *European Biophysics Journal*, 19, 311–316 (1991).
Bradley et al., "Mechanism of Multidrug Resistance", *Biochimica et Biophysica Acta*, 948, 87–128 (1988).
Moscow et al., "Multidrug Resistance", *Journal of the National Cancer Institute*, 80, 14–20 (1988).
Skovsgaard, "Mechanisms of Resistance to Daunorubicin in Ehrlich Ascites Tumor Cells", *Cancer Research*, 38, 1785–1791 (1978).
Inaba et al., "Active Efflux of Daunorubicin and Adriamycin in Sensitive and Resistant Sublines of P388 Leukemia", *Cancer Research*, 39, 2200–2203 (1979).
Tsuruo et al., "Increased Accumulation of Vincristine and Adriamycin in Drug–Resistant P388 Tumor Cells Following Incubation with Calcium Antagonists and Calmodulin Inhibitors", *Cancer Research*, 42, 4730–4733 (1982).

Tsuruo et al., "Overcoming of Vincristine Resistance in P388 Leukemia In Vivo and In Vitro through Enhanced Cytotoxicity of Vincristine and Vinblastine by Verapamil", *Cancer Research*, 41, 1967–1972 (1981).
Biedler et al., "Altered Plasma Membrane Glycoconjugates of Chinese Hamster Cells with Acquired Resistance to Actinomycin D, Daunorubicin, and Vincristine", *Academic Press, Inc.*, 453–482 (1981).
Kartner et al, "Cell Surface P–Glycoprotein Associated with Multidrug Resistance in Mammalian Cell Lines", *Science*, 221, 1285–1288 (1983).
Kartner et al., "Detection of P–Glycoprotein in Multidrug–Resistant Cell Lines by Monoclonal Antibodies", *Nature*, 316, 820–823 (1985).
Hamada et al., "Purification of the 170–to 180–Kilodalton Membrane Glycoprotein Associated with Multidrug Resistance", *The Journal of Biological Chemistry*, 263, 1454–1458 (1988).
Di Marco et al., "Adriamycin (NSC–123,127): A New Antibiotic with Antitumor Activity", *Cancer Chemotherapy Reports*, 53, 33–37 (1969).
Lozzio et al., "Human Chronic Myelogenous Leukemia Cell–Line with Positive Philadelphia Chromosome", *Blood*, 45, 321–334 (1975).
Tsuruo et al., "Characteristics of Resistance to Adriamycin in Human Myelogenous Leukemia K562 Resistant to Adriamycin and in Isolated Clones", *Jpn. J. Cancer Res. (Gann)*, 77, 682–692 (1986).
Gigli et al., "Correlation between Growth Inhibition and Intranuclear Doxorubicin and 4'–Deoxy–4'–iododoxorubicin Quantitated in Living K562 Cells by Microspectrofluorometry", *Cancer Research*, 49, 560–564 (1989).
Gigli et al., "Quantitative Study of Doxorubicin in Living Cell Nuclei by Microspectrofluorometry", *Biochmica et Biophysica Acta*, 950, 13–20 (1988).
Wilson, "Confocal Microscopy", *Academic Press Limited*, 1–64 (1990).

(List continued on next page.)

*Primary Examiner*—Donald E. Czaja
*Assistant Examiner*—Jane Williams
*Attorney, Agent, or Firm*—Hoffmann & Baron

[57] ABSTRACT

A method is described to determine multidrug resistance in living cells by laser scanning confocal fluorescence microscopy of doxorubicin in sensitive and resistant tumor cells. The intracellular distribution of doxorubicin in K562 cells has been studied by laser scanning confocal fluorescence microscopy. A different fluorescence pattern has been observed in sensitive and resistant cells. An intense fluorescence signal is evident on the plasma membrane of K562R cells with multidrug resistance. The fluorescence imaging of the drug offers then a new method—non destructive—to discriminate between sensitive and resistant cells, with high potential in the diagnosis of resistance in tumors in vivo. The differences in the intracellular drug distribution, as seen by laser scanning confocal fluorescence microscopy, moreover offer new indications on the mode of action of the drug in the living cell.

5 Claims, 6 Drawing Sheets

OTHER PUBLICATIONS

Gervasoni et al., "Subcellar Distribution of Daunorubicin in P–Glycoprotein–positive and —Negative Drug–resistant Cell Lines Using Laser–Assisted Confocal Microscopy", *Cancer Research*, 51, 4955–4963 (1991).

Lipsky et al., "A Vital Stain for the Golgi Apparatus", *Science*, 228, 745–747 (1985).

Willingham et al., "Immunocytochemical Localization of P170 at the Plasma Membrane of Multidrug–Resistant Human Cells", *The Journal of Histochemistry and Cytochemistry*, vol. 35, 1451–1456 (1987).

Brandes et al., "The Reaction of Acridine Orange with Proteoglycans in the Articular Cartilage of the Rat", *Histochemical Journal*, 22, 106–112 (1990).

Bucana et al., "Uptake and Accumulation of the Vital Dye Hydroethidine in Neoplastic Cells", *The Journal of Histochemistry and Cytochemistry*, 34, 1109–1115 (1986).

Weaver et al., "Laser Scanning and Confocal Microscopy of Daunorubicin, Doxorubicin, and Rhodamine 123 in Multidrug–Resistant Cells", *Experimental Cell Research*, 196, 323–329 (1991).

METHOD FOR THE DIAGNOSIS OF MULTIDRUG RESISTANCE IN LIVING CELLS

FIELD AND BACKGROUND OF THE INVENTION

A major obstacle in cancer chemotherapy is the emergence of resistance to cytotoxic drugs in tumor cells during treatment. Two central problems are still open: 1) the understanding at molecular level of the mechanism by which cells develop resistance; 2) the acquisition of a simple and rapid method for the diagnosis of resistance in cancer chemotherapy.

The resistant phenotype is characterized by a loss of sensitivity not always against a single drug, but towards a number of chemically unrelated molecules, a behavior known as "Multidrug resistance" (MDR) (1,2).

This complex mechanism is characterized by a reduced intracellular accumulation of the drug resulting from an increased efflux across the plasma membrane (3–5) or from an energy-dependent permeability barrier, which controls the drug entry.(6–9). These mechanisms involve a change in the cell phenotype, which appears at the plasma membrane level. Indeed an altered plasmalemmal composition characterizes MDR cells, with changes in the surface glycoproteins and overexpression of a P-glycoprotein, of molecular weight=170–180kD(8,10).

Several changes in the cell molecular architecture have been recognized (1); however plasma membrane alterations remain the distinctive characteristics of MDR.

DESCRIPTION OF THE INVENTION

In this report we suggest that differences in the intracellular drug distribution, as seen by confocal fluorescence microscopy, could offer a simple and crucial test to characterize resistant and sensitive tumor cells, and give new insights into the mode of action of the drug in living cells.

Although a great deal has been learned about doxorubicin, an antitumoral antibiotic belonging to the antracycline class, the intracellular distribution of the drug—at pharmacological concentrations—is not yet known at the spatial resolution now allowed by confocal microscopy. We present here confocal fluorescence imaging data of doxorubicin in human leukemia K562 cells (12), a well known biological model of multidrug resistance for its strong refractoriness to doxorubicin and overexpression of the membrane P-glycoprotein (13).

The laser scanning confocal fluorescence microscope MRC-600 (Lasersharp, Bio-Rad Microscience Division) was coupled to an epifluorescence microscope. An Argon laser was used for excitations at 488 nm and 515 nm, falling within the broad visible absorption band of doxorubicin (11,14). Fast photon counting mode has been employed to detect the drug fluorescence signal, through a long pass filter in the emission fluorescence band of the drug, above 515 nm (14). The high sensitivity of the photon counting detection allowed :1) to keep laser excitation at low power (<0.1 mW), preserving cell viability during measurements, and 2) to collect high quality images from low drug concentrations, in the range of pharmacological significance. A high level of confocality has been kept in the optics. In this way it has been possible to image the cell within a narrow depth of focus (0.5 µm) and to obtain optical-section images in the Z-direction, together with a very high spatial resolution in the image plane (15). K562 sensitive and resistant cells (12,13) in exponential growth phase (105 cells/ml) were incubated for 1 hour in culture medium containing doxorubicin (DXR) (Farmitalia- Carlo Erba, Milan, Italy; and Roger Bellon Laboratories, Paris, France) at a concentration varying from 2 to 0.01 µM. Cells were washed twice and resuspended in PBS.

Figure 2A:

Oil immersion objective, with 60× magnification and N.A. 1.4, in the epi-illuminated microscope coupled to the MRC-600 system was employed for measurements on living cells. In FIG. 1 and 2a are reported the fluorescence images of K562 S living cells, incubated for 1 hour at 0.1 µM and at 0.01 µM respectively. A non homogeneous drug fluorescence can be recognized within the nucleus. The highest nuclear fluorescence appears in the perinuclear region, as recently reported also for daunorubicin when cells are examined under living conditions(16).

No membrane fluorescence is observed in sensitive cells, at any drug concentration and at any time after incubation. A brilliant fluorescence is instead observed in the K562 S cytoplasm. This sharp signal, evident only in living cells, can be attributed to the Golgi membranes system of the cell. This is easily seen by comparison with the data of Lipsky and Pagano (17) on C6-NBD-ceramide, a vital stain of the Golgi apparatus. Indeed, this signal is present only when the Golgi element belongs to the focal plane of the image; it is enough to move the focus of about 4 µm in the Z-direction in order to eliminate completely its fluorescence from the image. This is shown for K562 R cells incubated for 1 hour in a 0.01 µM doxorubicin solution in FIG. 3a and 3b where two optical sections 4 µm apart are reported. Moreover it is interesting to remark that the spatial resolution of the confocal images (15) allows the examination of the Golgi morphology in the living cell by means of doxorubicin, that can be seen therefore as a vital fluorescent stain of this organelle. We add a final comment on the images of sensitive cells concerning the drug fluorescence in the cytoplasm, where ordered filamentary structures can be frequently seen (FIG. 1). Although it is impossible at this stage to recognize these structures, they are an indication of the plurality of drug interactions in the cell.

Considering now the results obtained on resistant living cells, the doxorubicin pattern is very different from that observed on sensitive living cells.

Figure 2B:

If we compare the data of FIG. 2a and FIG.2b (see also FIG. 1) a major difference is apparent in the nuclear region, where almost no fluorescence is observed in resistant cells in agreement with the results reported for daunorubicin in reference 16. This is also confirmed by the Z-sectioning study. (FIG. 4)

Figure 3A:
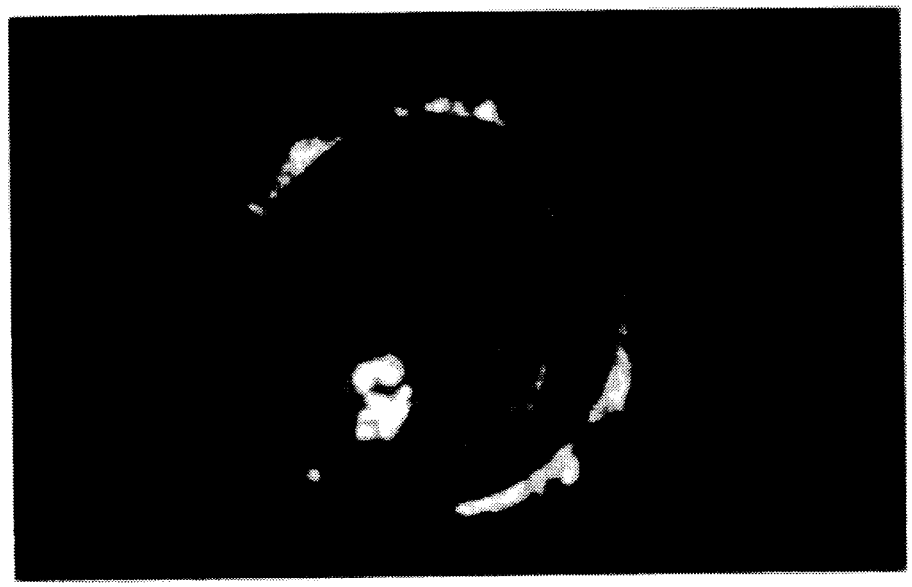

A second important difference between sensitive and resistant cells is the intense fluorescence of the plasma membrane of resistant cells, as shown in FIG. 2a and 2b, where the images of K562S and R cells treated with doxorubicin at 0.01 µM for 1 hour are reported. The membrane fluorescence is not homogeneously distributed along the membrane, with evident filaments emerging into the extracellular medium. A bright fluorescence of the Golgi system is also evident in resistant cells, when this organelle belongs to the image plane. (FIG. 3a and b)

A further important detail in the fluorescence of resistant cells is the pattern of weak fluorescent spots, regularly distributed in defined areas of the cytoplasm.(FIG. 2b, 2a, and 3b) This pattern of spot-like signals varies with drug concentration and with time after the incubation. This "punctuate pattern", observed also in tumor cells resistant to daunorubicin, has been suggested (16) to be a characterizing feature of resistance In the case of Multidrug Resistance examined here, with overexpression of membrane P-glycoprotein, the characterizing feature of resistance is the bright fluorescence of plasma membrane. In K562R cells treated with doxorubicin this membrane fluorescence can be detected by laser scanning confocal fluorescence microscopy, in the range of drug concentrations of pharmacological significance. The same membrane fluorescence in K562R can also be induced by other vital dyes such as acridine orange (19) and dihydro-ethidium (20) and fluorescent probes and cations such as ethidium bromide, propidium and rhodamine 123 (21).

This result is in agreement with the localizations proposed for the P-glycoprotein (18), which is found in the plasma membrane, with highest concentration, and in the luminal side of the Golgi membranes, as expected for a transport protein. The doxorubicin fluorescent pattern of the multi-drug resistant cells appears then to coincide with the P-glycoprotein localization.

The differences on the drug fluorescence patterns in sensitive and resistant K562 cells suggest, therefore, a simple and rapid method to detect multidrug resistance in tumor cells (and particularly in leukemia). The non-destructive character of this technique indicates possible applications in the screening of tumors in vivo, an important goal in cancer chemotherapy.

REFERENCES

1) G. Bradley, P. F. Juranka and V. Ling, BBA 948, (1988) 87–128
2) J. A. Moscow, K. H. Cowan, J. Nat. Cancer Institute 80, (1988) 14–20.
3) T. Skousgaard, Cancer Research 38, (1978) 1785–1791.
4) M. Inaba, H. Kobaiyashi, Y. Sakurai, and R. K. Johnson, Cancer Res. 39 (1979) 2200–2203.
5) T. Tsuruo, H. Ida, S. Tsukagoshi, and Y. Sakurai, Cancer Research 41 (1981) 1967–1972; idem CancerResearch 42 (1982) 4730–4733.
6) V. Ling, Carlsen S. A. and Y. P. Yee in "Membrane toxicity" (Miller, M. W. and Shamoo Eds.) Plenum Press (1977) pp. 247–264.
7) J. L. Biedler,and R. H. F. Peterson in "Molecular Actions and Targets for Cancer Chemiotherapeutic Agents" (A. C. Sartorelli, J. S. Lazo, and J. R. Bertino Eds.) Academic Press (1981) pp. 453–482.
8) N. Kartner, J. R. Riordan, G. Bradley, and V. Ling, Science 221 (1983) 1285–1288.
9) N. Kartner, D. Evernden-Porelle, G. Bradley, and V. Ling, Nature 316 (1985) 820–823
10) H. Hamada and T. Tsuruo, J. Biol. Chem. 263 (1988) 1454–1458
11) A. Di Marco, Cancer chemother. Rep. 32 (1975) 48
12) C. B. Lozzio and B. B. Lozzio, Blood 45 (1975) 321–334
13) T. Tsuruo et al., Jpn. J. Cancer Res. 77 (1986) 682–692
14) M. Gigli, S. M. Doglia, J. M. Millot, L. Valentini and M. Manfait, BBA 950 (1988) 13; M. Gigli et al., Cancer Res. 49 (1989) 560.
15) Confocal Microscopy, Ed: T:Wilson, Academic Press (1990)
16) J. E. Gervasoni, Jr. et al., Cancer Research 51,4955(1991).
17) N. G. Lipsky and R. Pagano, Science 228, 745 (1985)
18) M. C. Willingham et al., J. Hist. and Cytochem. 88, 1451 (1987)
19) G. Brandes and E. Reale, Histochem. Journal, 22, 106–112 (1990)
20) C. Bucana, I. Saiki, and R. Nayar, J. Hist. and Cytochem. 34, 1109–1115 (1986)
21) J. L. Weaver, P. S. Pine, A. Aszalos, P. V. Schoenlein, S. J. Currier, R. Padmanabhan, and M. M. Gottesman, Exp. Cell Research, 196, 323–329 (1991)

FIGURE CAPTIONS

FIG. 1: Confocal fluorescence image of DXR in K562S living cell in suspension, incubated for 1 hour in DXR 0.1 µM collected by fast photon counting mode with Argon laser excitation at 488 nm and emission through Long Pass filter 515 nm, (accumulation of 900 frames).

FIG. 2: Confocal fluorescence image of DXR in living cells in suspension, incubated for 1 hour in DXR 0.01 µM, collecting conditions as in FIG. 1: a) K562S accumulation of 323 frames; b)K562R accumulation of 320 frames.

Figure 3B:
Figure 4A:
Figure 4B:
Figure 4C:
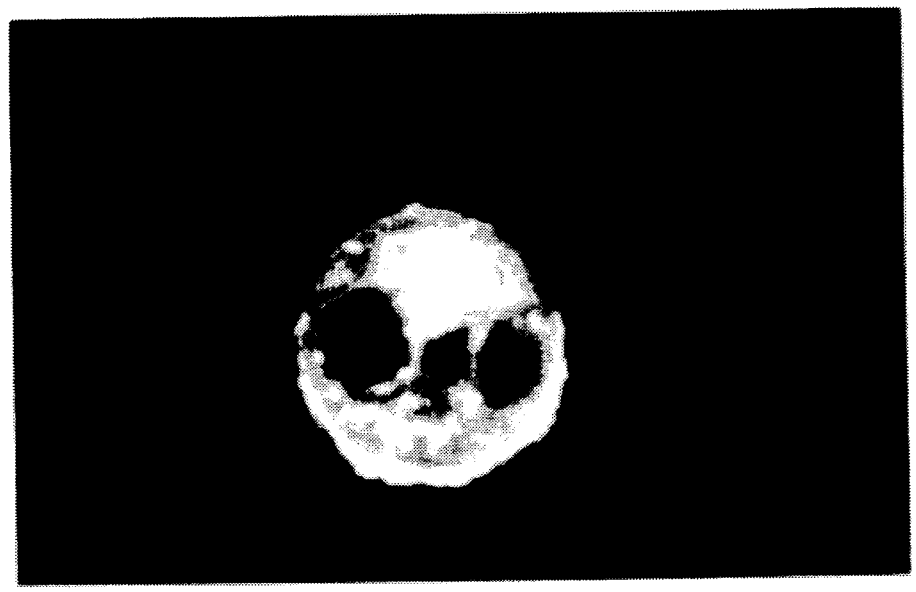
Figure 4D:
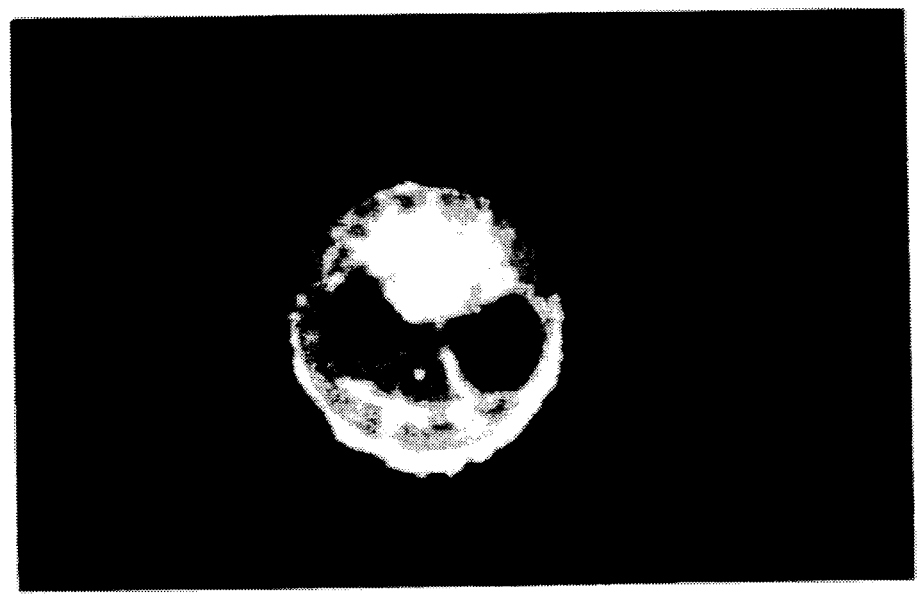
Figure 4E:
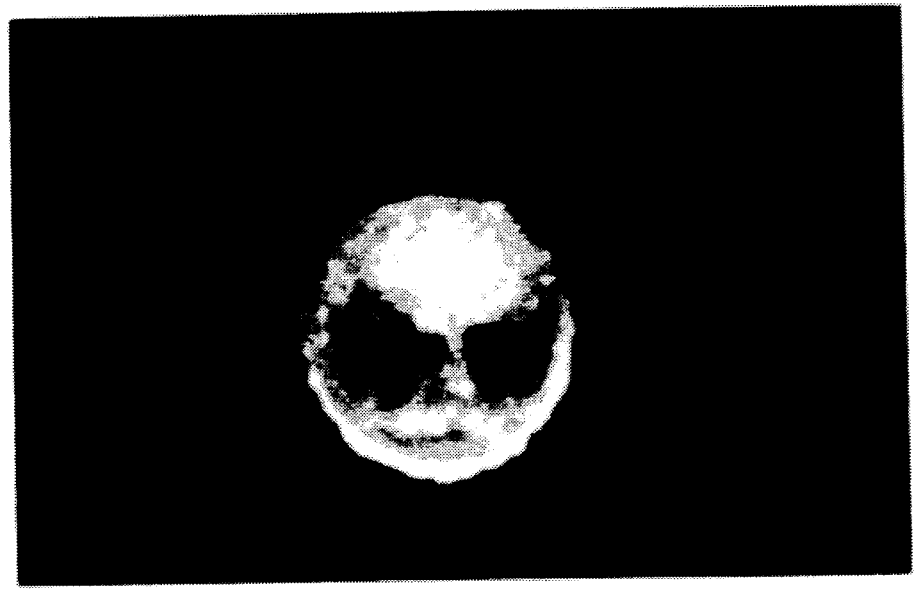
Figure 4F:

FIG. 3a and 3b: Confocal fluorescence image of DXR in living K562R cell in suspension, incubated for 1 hour in DXR 0.01 µM, collecting conditions as in FIG. 1 (accumulation of 320 frames): a) the focal plane of the image is adjusted on the Golgi element of the cell; b) the focal plane is moved 4 µm above.

FIG. 4a, 4b, 4c, 4d, 4e, 4f: Z-sectioning fluorescence images of K562R living cells incubated in DXR 0.1 µM for 1 hour; series of images at planes with separation distance of 2 µm. Accumulation of 150 frames (collecting conditions as in FIG. 1 ).

We claim:

1. A method to determine Multidrug Resistance in living tumor cells, comprising: determining an intracellular distribution of doxorubicin in living cells of the K562 cell line through analysis of differences in fluorescent patterns of sensitive and resistant cells, obtained by laser scanning confocal fluorescence microscopy.

2. A method as recited in claim 1, wherein the living tumor cells employed are human leukemia cells of type K562.

3. A method as recited in claim 1, wherein said Multidrug Resistance is indicated by a presence of an intense fluorescent signal on the living tumor cells' plasma membranes.

4. A method as recited in claim 3, wherein the fluorescent signal on the living cells' plasma membrane is detected by confocal fluorescence microscopy, thereby allowing collection of images of living tumor cells' optical sections in a z-axis direction.

5. A method as recited in claim 3, wherein the membrane fluorescence of multidrug resistant cells may be further detected by a fluorescent compound selected from the group consisting of acridine orange, dihydro-ethidium, ethidium bromide, propidium bromide and rhodamine 123.

* * * * *